United States Patent [19]
Kataoka et al.

[11] Patent Number: 5,374,266
[45] Date of Patent: Dec. 20, 1994

[54] MEDICAL LASER TREATMENT DEVICE

[75] Inventors: Kenzo Kataoka; Odaka Masaki; Yoshihide Okagami; Akira Yuba, all of Kyoto; Sadahiro Nakajima; Naoshi Endo, both of Tokyo, all of Japan

[73] Assignees: Kabushiki Kaisha Morita Seisakusho, Kyoto; Hoya Corporation, Tokyo, both of Japan

[21] Appl. No.: 982,082

[22] Filed: Nov. 25, 1992

[30] Foreign Application Priority Data

Nov. 27, 1991 [JP] Japan ................ 3-339761
Nov. 27, 1991 [JP] Japan ................ 3-339763
Nov. 27, 1991 [JP] Japan ................ 3-339765

[51] Int. Cl.$^5$ ............................. A61B 17/36
[52] U.S. Cl. ........................... 606/15; 606/13; 606/14; 604/21
[58] Field of Search ................ 128/395–398; 606/10, 13–17; 604/20, 21; 385/39, 50, 55, 74, 92, 94

[56] References Cited

U.S. PATENT DOCUMENTS

| | | | |
|---|---|---|---|
| 4,676,242 | 6/1987 | Doi | 606/16 |
| 4,826,431 | 5/1989 | Fujimura | 606/14 |
| 4,832,024 | 5/1989 | Boussignac et al. | 128/395 |
| 4,988,163 | 1/1991 | Cohen et al. | 128/397 |
| 5,074,861 | 12/1991 | Schneider et al. | 606/17 |

Primary Examiner—Stephen C. Pellegrino
Assistant Examiner—M. Peffley
Attorney, Agent, or Firm—Koda and Androlia

[57] ABSTRACT

A medical laser treatment device comprising a laser generation source and a laser handpiece which comprises a light-guiding fiber used to guide a laser beam irradiated from the laser generation source, a probe for guiding the laser beam having been guided by the fiber to an object to be irradiated, at least two independent air supply passages and at least one water supply passage, the laser handpiece being adapted such that the emission end of the light-guiding fiber is airtightly isolated from the incident end of the probe via a light-guiding shield plate to make the internal section of the light-guiding fiber airtight, to cool the emission end of the light-guiding fiber using dry gas supplied from the first air supply passage and to cool the incident end of the probe using gas supplied from the second air supply passage, and being also arranged such that water supplied from the water supply passage is blown out from the peripheral section of the leading end of the probe, thereby preventing the emission end of said light-guiding fiber from absorbing moisture and being heated.

19 Claims, 8 Drawing Sheets

MEDICAL LASER TREATMENT DEVICE

TITLE OF THE INVENTION

1. Field of the invention

The present invention relates to a medical laser treatment device including medical laser handpiece.

2. Prior Art

Laser handpieces have conventionally been used widely for medical and dental treatments to transpire and cut out living tissues, to coagulate blood and stop bleeding, or to heat living tissues and ease pain, and they have produced intended medical effects. For the conventional laser handpieces, a carbon dioxide excitation laser and a Nd:YAG solid laser have been used as lasers to treat soft tissues, such as internal organ tissues, muscles and skins. In the dental treatment field, the above-mentioned lasers have been used to cure periodontal disease which is caused at soft tissues around teeth.

The handpieces used for these applications are generally classified into contact and non-contact type handpieces. In the case of the former type, the end of the probe provided at the leading end the handpiece, which irradiates a laser beam, is directly contacted to an affected portion and the laser beam which has passed through the probe is irradiated. In the case of the latter type, wherein the laser irradiation port provided at the leading end of the handpiece is placed away from the affected portion and a laser beam is irradiated from the laser irradiation port to the affected portion.

At the time of laser irradiation, cooling gas is blown out or water is poured to the affected portion to prevent the affected portion from being overheated or to cool the tissues around the affected portion, which should not be heated. In particular, in the case of the contact type laser handpiece, the laser probe thereof, through which the laser beam passes and is irradiated while the probe is in contact with the affected portion, that is, a cylindrical or conical chip usually made of transparent glass or synthetic resin, is heated and damaged because of breakage or melting or is stained with deposits, resulting in improper irradiation. To solve these problems, water is flown or poured to the chip to cool and clean tile leading end of the chip.

These days, dental treatment technologies using laser beam irradiation have been examined and attempts have been made to develop laser treatment devices for various treatments of the hard tissues of teeth, such as the removal of areas of dental caries, the removal of dentin or the cut-off of enamel. Conventional treatment devices using carbon dioxide lasers have the following problems: Carbonization is apt to occur because of the significant absorption of the laser beam irradiated to the surfaces of tooth tissues. In addition, when cooling water is used, because of the high laser beam absorption characteristic of water, the laser energy is absorbed only by the water layer formed on the tissue surface and the laser beam does not reach the affected portion of the tooth tissue, making proper treatment difficult. Furthermore, a manipulator comprising a light-guiding pipe has been used conventionally to irradiate a carbon dioxide laser beam, making the maneuverability of the device lower.

It has been recognized that the Nd:YAG solid laser has an effect of transpiring hard tissues of tooth substance due to the use of pulse waves. A dental treatment device using the Nd:YAG solid laser has already been proposed (Japanese Laid-open Patent Application No. 2-500833). Although this laser can be used to remove enamel, since the absorption rate of the laser beam having a wavelength of 1.06 $\mu$m to the tooth substance is small, the transpiration effect of the laser beam is very low and the cutting speed by the laser beam is slow. In addition, the laser beam penetrates the inside sections of the tooth tissues and generates heat, causing heat damages at tooth sections. Furthermore, the laser beam is almost ineffective in treating thin enamel.

On the contrary, since an Er:YAG solid laser has high processability for the tooth substance, it has attracted attention for tooth treatment and a treatment device using the laser beam generated by this laser has been proposed (Japanese Laid-open Patent Application No. 2-504478). The laser beam generated by this Er:YAG solid laser is infrared rays having a wavelength of 2.94 $\mu$m. The laser beam excites OH radicals and has an extremely high absorption rate for living tissues including OH radicals. In the dental Field, it is recognized that the laser beam has an effect of transpiring hard tissues including OH radicals such as teeth. By using this property, the irradiation of the Er:YAG solid laser beam is gradually being used to cut teeth and remove tartar.

The applicants of the present invention have already proposed a contact type laser treatment device which can also use the Er:YAG solid laser beam, more particularly, a device comprising a replaceable fiber probe capable of etching initially areas of dental caries, such as Forming cavities in teeth, treating pulp canals and removing tartar as well as stopping bleeding and performing cut-out operation at soft tissues (Japanese Laid-open Patent Application No. 3-211837).

Glass fibers, such as a Fluoride fiber, a chalcogenide glass fiber and a quartz glass fiber, and crystal fibers, such as a sapphire fiber and a zinc selenium fiber can be used as optical fibers for guiding the laser beam generated from the Er:YAG laser to laser treatment devices such as laser handpieces. Among these fibers, the fluoride fiber is best suited because of its high laser beam transmission efficiency.

In the conventional contact type laser handpiece used to treat soft tissues, since its laser irradiation probe, that is, its chip is heated, water is poured to the external circumference of the chip or to water-supply holes provided in the chip to cool the chip itself and the affected portion irradiated by the laser beam. When the chip is used to process teeth, however, since the leading end of the chip has a circular cylindrical or conical shape, the chip is not suited for precision processing, such as forming cavities in teeth. In addition, if the leading end is damaged by breakage of melting, the laser beam is scattered and cannot be converged, disabling the use of the chip.

When a light-transmission fiber probe is used for the laser beam irradiation probe as described above, the probe must be cooled to prevent its leading end from being heated. In the case of the probe comprising a fiber, it is difficult to efficiently cool the external cirumference of the above-mentioned chip having a short conical shape, because water separates and drops from the surface of the fiber.

In the case of the device for treating hard teeth by irradiating the Er:YAG laser beam, the fluoride fiber having a high laser beam transmission rate first exhibits a hydroscopic property and is deteriorated when it absorbs moisture. The fiber is then heated by laser transmission, causing a serious problem of the breakage of the fiber. This is because it is difficult to provide a proper moisture prevention coating, which does not hinder the transmission of the laser beam, at the leading end surface of the fiber, although the external circumference of the fiber is coated with a jacket to prevent moisture absorption Next, when treating teeth, hard tissues, by using the Er:YAG laser beam, the probe is required to be inserted into the narrow gap portions and the thin canal portions of teeth and to perform drilling efficiently. Consequently, the fiber probe used for treating teeth must have a shape and a structure matched to the portions and conditions of the teeth to be treated.

Although this kind of the contact type laser handpiece is convenient for depth adjustment during operation, if the leading end of the probe is broken when the probe is used, the irradiation pattern of the laser beam is disturbed and tooth substance processing accuracy is deteriorated.

Transpiration residues attach to a tooth while the laser beam is irradiated to the tooth. To remove the transpiration residues attached to the tooth and to promote transpiration and scattering at the irradiated tooth portion, tile water being present on the surface of the tooth portion functions effectively. It is therefore necessary to find out a means to efficiently supply water to clean and cool the surface of the tooth when adopting a fiber probe.

Moreover, the enamel which is not transpired but remains after the Er:YAG solid laser beam is irradiated once is coated with a layer lacking OH radicals included in hydration shell. Even when the laser beam is irradiated again, it is difficult to cut the layer, resulting in a problem of reduced processing performance.

SUMMARY OF THE INVENTION

The present invention provided to solve the above-mentioned problems is categorized into first, second and third inventions depending on the purposes described below.

The first object of the present invention is to provide a medical laser treatment device capable of irradiating a laser beam from the leading end of the handpiece thereof, spraying cleaning water and isolating a light-guiding fiber, which is apt to be adversely affected by moisture, From moisture and sprayed water to prevent the adverse effect of the moisture.

To accomplish this object, the laser handpiece of the medical laser treatment device of the first invention basically comprises a light-guiding laser fiber extending from a laser generator and an irradiation probe, wherein the fiber and the probe are arranged such that the fiber is isolated so as not to be wet with water supplied to the probe inside the handpiece and such that the fiber is connected to the probe to allow the laser beam to be guided. (See claims 1 to 3.)

The second object of the present invention is to provide a medical laser treatment device, the laser handpiece of which comprises a probe having a shape suited for laser beam irradiation treatment portions and conditions and is able to effectively pour water to the treatment portions and the leading end of the probe.

To accomplish the second object, the handpiece of the second invention has the structure of the first invention as a premise, and the irradiation probe thereof is a fiber probe and comprises a probe protection pipe, into which the Fiber probe is inserted, to provide a water supply passage. (See claims 4 to 9.)

The third object of the present invention, that is, the third invention, is not only to remove dental caries portions and dentin but also to perform conventionally difficult processes such as cutting off enamel, forming cavities and removing tartar by using laser beam irradiation, and to provide a laser treatment device which does not cause heat trouble at affected tooth portions and peripheral tissues during laser treatment using the Er:YAG solid laser, thereby preventing the processing efficiency of the device from being reduced by poured water and attached non-transpired substances. (See claims 10 and 11.)

The above-mentioned and other objects and features of the present invention will be fully understood through the following detailed explanations referring to the drawings attached to illustrate examples.

BRIEF DESCRIPTION OF THE DRAWINGS

FIG. 1 is a vertical sectional view taken on line I—I in FIG. 3; FIG. 2 is a vertical sectional view of the laser handpiece taken on line II—II in FIG. 3; FIG. 3 is a transverse sectional view of the laser handpiece taken on line III—III in FIG. 1.

DETAILED DESCRIPTION OF THE INVENTION

Figure 1:
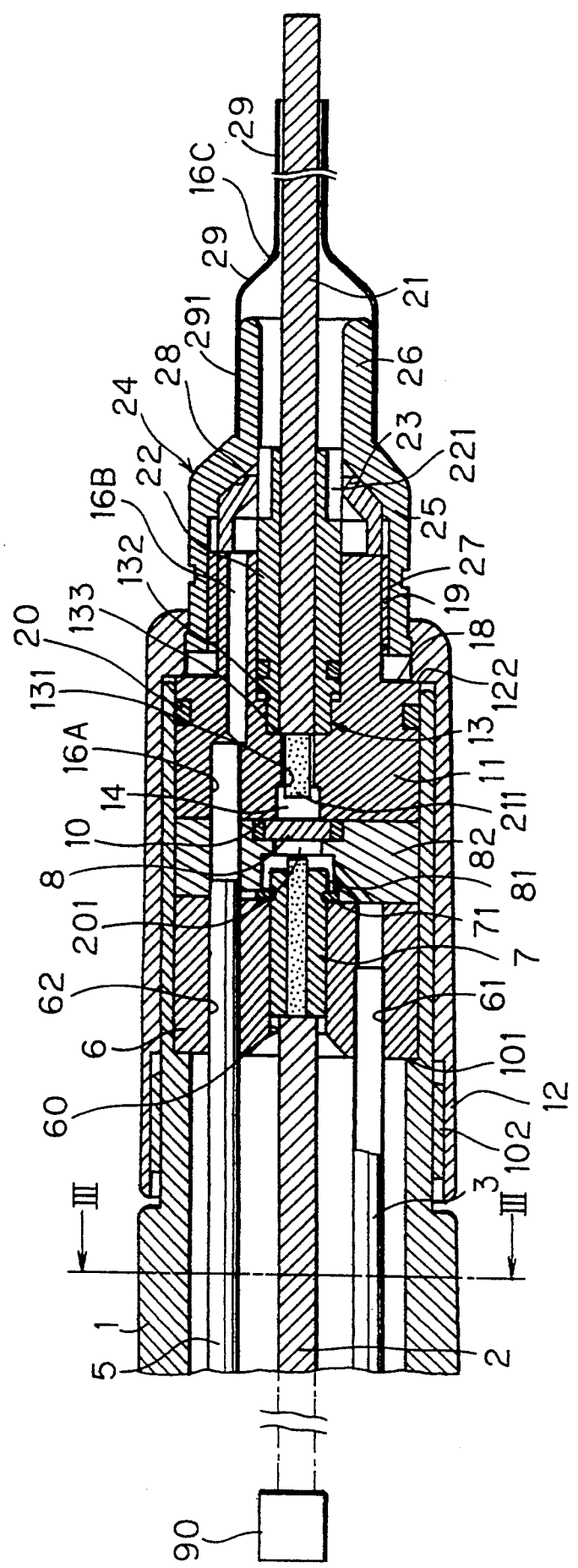
FIGS. 1 to 3 are sectional views illustrating a laser handpiece of a dental laser treatment device of an example commonly used for the first, second and third inventions.

The medical laser treatment device of the first invention constituting the basic invention, comprises a laser generation source and a laser handpiece which comprises a light-guiding fiber used to guide a laser beam irradiated from the laser generation source, a probe for guiding the laser beam having been guided by the fiber to an object to be irradiated, at least two independent air supply passages and at least one water supply passage, the laser handpiece being adapted such that the emission end of the above-mentioned light-guiding fiber is airtightly isolated from the incident end of the probe via a light-guiding shield plate to make the internal section of the light-guiding fiber airtight, to cool the emission end of the light-guiding fiber using dry gas supplied from the first air supply passage and to cool the incident end of the probe using gas supplied from the second air supply passage, and being also arranged such that water supplied from the water supply passage is blown out from the peripheral section of the leading end of the probe.

The medical laser treatment device of the second invention comprises a probe protection pipe, the base section of which is removably fit and connected to the front section of the handpiece of the above-mentioned first invention to allow water to pass through the above-mentioned water supply passage so that the gap between the internal surface of the probe protection pipe and the external surface of the probe is used as a water passage for supplying water to the leading end of the probe.

Furthermore, the third invention is a dental laser treatment device according to the first invention wherein the laser generation source thereof is a laser generator for generating an Er:YAG solid laser beam, the light-guiding fiber thereof is a fluoride light-guiding fiber and the device is equipped with a laser control means for adjusting the laser output of the laser generator.

According to the structure of the laser treatment device of the first invention, the laser beam generated from the laser generation source is emitted from the emission end of the light-guiding fiber, penetrates the light-guiding shield plate, enters the incident end of the probe and is irradiated from the leading end of the probe to an affected portion to be treated. Since the section accommodating the light-guiding fiber is made airtight by airtightly isolating the emission end of the light-guiding fiber from tile incident end of the probe via the light-guiding shield plate, the emission end surface of the light-guiding fiber is not made contact or dampened with the water supplied to the probe from the water passage. In addition, since the emission end surface is isolated from the outside air, it does not absorb the moisture included in the air. Furthermore, since the emission end of the light-guiding Fiber is cooled by the dry gas supplied from the first air supply passage, the emission end surface of the light-guiding fiber is maintained in a dry condition at all times while the laser handpiece is used, and at the same time the heat generated on the emission end surface during laser transmission can be removed by cooling. As a result, a fiber which is easily deteriorated by moisture absorption can be used as the light-guiding fiber. Since the moisture absorbing light-guiding fiber is isolated from the probe, the probe can be made attached and detached so that it can be replaced as desired. Moreover, the water from the second water supply passage is used to cool and clean the leading end of the probe and the affected portion to be treated. Since the incident end surface of the probe is cooled and dried by the gas supplied from the second air supply passage, the water drops coining out at the time of probe replacement are scattered and eliminated from the incident end surface and the surface of the light-guiding shield plate to dry the surfaces. The heat generated on the incident end surface at the time of laser transmission can also be removed by the gas.

According to the structure of the second invention, the leading end of the laser handpiece is removably equipped with a probe comprising a thin optical fiber. Since this fiber probe is inserted into the probe protection pipe removably installed at the leading end thereof, the laser beam can be irradiated while the leading end of the fiber probe is placed close to a target tooth or a portion to be treated. In this case, the optical fiber is protected by the protection pipe and there is little danger of breakage. The fiber can thus be made very thin, being suited for insertion into the narrow deep section of the probe. Since an appropriate gap is formed between the external circumference of the fiber probe and the internal circumference of the probe protection pipe, and the gap communicates with the above-mentioned water supply passage provided in the handpiece at the leading end of the handpiece wherein the base end section of the probe protection pipe is installed, the gap can be used as a water passage. Accordingly, the external circumference and the leading end of the fiber probe can be cooled positively by the water flowing in the probe protection pipe and at the same time the water can be sprayed or discharged effectively to the laser beam irradiation portion, thereby effectively preventing the irradiation portion from being overheated or effectively transpiring the hard tissues of the irradiation portion. When a flexible fiber is used for the optical fiber of the fiber probe, the fiber probe can easily have a desired shape by making the probe protection pipe in a desired shape, straight or bent. With this structure, the laser beam irradiation direction from the probe to the handpiece unit can be adjusted as desired by simply replacing the probe protection pipe.

According to the structure of the third invention, the Er:YAG solid laser beam generated from the laser generator is transmitted to the handpiece via the fluoride light-guiding fiber, and guided to the fiber probe installed at the leading end of the handpiece. The laser beam is then irradiated from the leading end of the fiber of the fiber probe to the tooth substance to be treated. The Er:YAG solid laser beam irradiated to the tooth substance is infrared rays with a wavelength of 2.94 $\mu$m and can be used to transpire the hard tooth substance of the dentin including the OH radicals and to cut off the tissues from the irradiated surface. Since the leading end of the fiber of the fiber probe is thin, 50 to 800 $\mu$m in diameter, the diameter of the laser beam irradiated from the irradiation end surface to the target portion is approximately equal to the diameter of the leading end of the fiber and the irradiation end surface can be inserted into the narrow deep section of the tooth to be treated. The surface of the irradiated tooth can thus be cut and small diameter cavities can be formed easily by manual operation of the handpiece. Furthermore, since the leading end of the fiber of the fiber probe is thin, the leading end of the fiber probe can be placed close to or in contact with the surface of the irradiated tissue having a rough surface easily and accurately. For these reasons, when water is poured from the vicinity of the leading end of the fiber probe, the water layer in the gap between the leading end of the fiber probe and the surface of the irradiated tissue becomes thin, the absorption rate of the laser beam to the water becomes low and the absorption efficiency of the laser beam to the irradiated tissue increases.

When the laser beam is irradiated to the tooth substance, particularly to the enamel, the transpiration at the time of reirradiation is lowered by the dense calcium layer being attached and remaining after the hydration shell on the enamel surface including the OH radicals is transpired. In the case of the third invention, however, the attached residues can be removed by the water poured to the irradiation surface and by the disturbance effect of cavitation caused by the intermittent irradiation of the pulse-like laser beam, thereby making it possible to maintain the high enamel transpiration efficiency.

EXAMPLE 1

Figure 2:
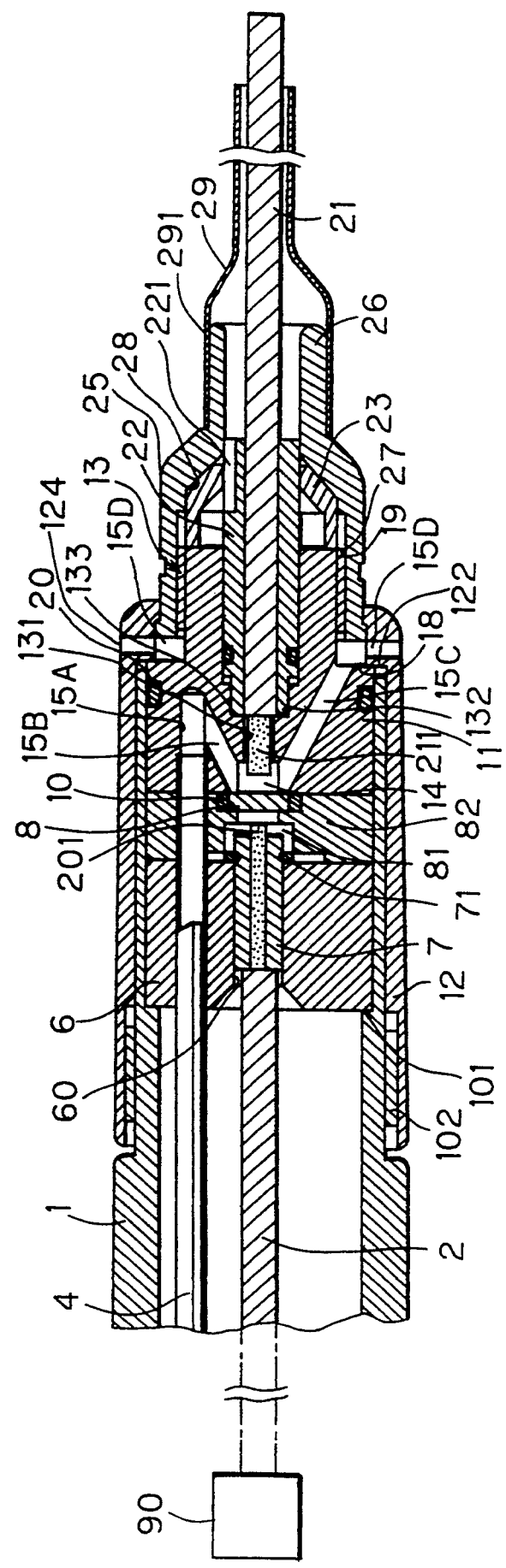
Figure 3:
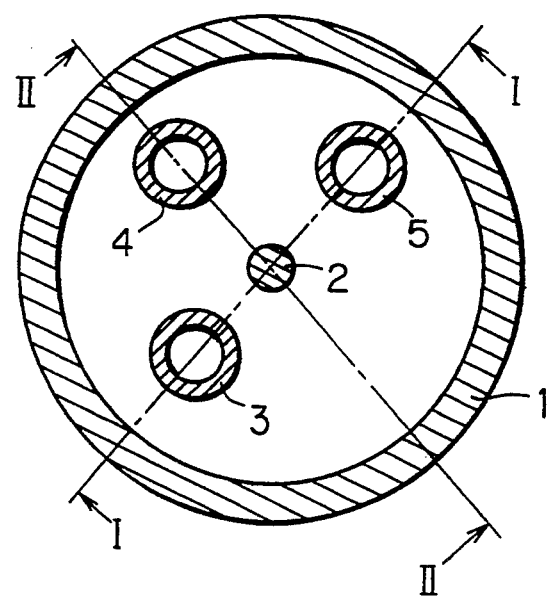

The example of the first invention is first explained referring to the drawings. FIG. 1 is a vertical sectional view of an example of the dental laser handpiece of the present invention, taken on line I—I in the transverse sectional view of FIG. 3. FIG. 2 is a vertical sectional view taken on line II—II in FIG. 3. FIG. 3 is a transverse sectional view taken on line III—III in FIG. 1.

In FIGS. 1 to 3, numeral 1 represents a handpiece unit, which includes a light-guiding fiber 2 for guiding the laser beam emitted from a laser generation source 90, a first air supply pipe 3, a second air supply pipe 4 and a water supply pipe 5.

The light-guiding fiber 2 is an optical fiber, whose core and clad are made of fluoride glass and which is coated with a protection jacket made of UV resin, for example.

In the inside and on the leading end side of the handpiece unit 1, a light-guiding fiber holder 6 is installed so that the fiber holder 6 contacts a step section 101 provided on the internal circumferential surface. On the leading end side of the holder 6, a light-guiding shield plate holder 82 is installed. In addition, on the leading end side of the light-guiding shield plate holder 82, a joint 11 is installed. By tightening a cover nut 12 which is engaged with the screw section 102 of the handpiece unit 1, the above-mentioned holders 6 and 82 and the joint 11 are secured between the step section 101 and the step section 122 of the cover nut 12.

The trailing end of the light-guiding fiber 2, which has not the protection jacket used to cover the light guiding fiber 2 but has a sleeve (ferrule) 7 attached thereto via adhesive for example, is inserted into the optical fiber insertion hole 60 of the light-guiding fiber holder 6. A ring 71 fit in a circumferential groove provided on the external circumference of the sleeve 7 contacts the end surface of the holder 6 to position the emission end 201 of the light-guiding fiber 2. With this structure, even when any distortion occurs between the handpiece unit 1 and the fiber 2, rotation generates between the sleeve 7 and the holder 6 to prevent the fiber 2 from being broken.

The light-guiding shield plate holder 82 has a concave chamber 81 for accommodating the above-mentioned emission end 201 of the light-guiding fiber 2 and a window section adjacent to the chamber 81, and the window section is equipped with a light-guiding shield plate 8, such as a condenser lens or an optical glass pane. The light-guiding shield plate 8 is airtightly supported by an O-ring 10. Consequently, the parts on both sides of the light-guiding shield plate 8, that is, the concave chamber (emission cooling chamber) 81 and the incident cooling chamber 14 of the joint 11 are airtightly isolated by the light-guiding shield plate 8. The interfere between the joint 11 and the handpiece unit 1 is also airtightly sealed by an O-ring 20 to make the section incorporating the light-guiding fiber 2 on the left side from the light-guiding shield plate 8 in the figure airtight and to isolate the light-guiding fiber 2 from the moisture in the air.

The opening end section of the first air supply pipe 3 is inserted into the through hole 61 of the light-guiding fiber holder 6 and secured by adhesive for example. The dry gas supplied from the first air supply pipe 3, usually dry air with its dew point being set as low as possible by a dehydrator, passes through the gap between the light-guiding fiber holder 6 and the light-guiding shield plate holder 82 from the through hole 61 and enters the emission cooling chamber 81 to cool the emission end 201 of the light-guiding fiber 2. The dry gas entered the emission cooling chamber 81 passes through the gap provided between the water supply through hole 62 of the holder 6 and the water supply pipe 5 and enters the gap among the handpiece unit 1, the light-guiding fiber 2 and the pipes 3, 4 and 5. In tile gap, the air flows backward to the left in the figure and is discharged from a gas discharge port (not shown) provided at a position fully away from the above-mentioned emission end 201. This gas discharge port has a one-way valve to prevent the external air from entering the section incorporating the light-guiding fiber 2.

Since the dry gas supplied from the first air supply pipe 3 cools the emission end 62 of the light-guiding fiber 2, flows backward in the section incorporating the light-guiding fiber 2 and then is discharged at a position fully away from the emission end 201, the dry gas flowing backward isolates the light-guiding fiber 2 from the moisture and has the effect of cooling the light-guiding fiber 2. Even if the light-guiding fiber 2 made of a fluoride fiber having relatively low breakage strength is broken, powder and smoke caused at the time of breakage are discharged to the outside at the position fully away from the emission end 201 by the above-mentioned flow of the dry gas. As a result, the light-guiding shield plate 8 is not stained by dust or smoke. Furthermore, the smoke and powder generated at the time of breakage do not contact the affected portion, preventing the patient from being frightened. In the first invention, it is desired that the position where the dry gas supplied from the first air supply pipe 3 is discharged, that is the position fully away from the emission end 201, should be selected from the above-mentioned point of view.

Although it has been explained that the light-guiding fiber 2 comprises a fluoride fiber in the above descriptions, the light-guiding fiber 2 is not limited to a fluoride fiber in the case of the first invention. The first invention is effectively applied not only to a fluoride fiber but also to an optical fiber having low moisture resistance and being easily apt to be adversely affected by moisture, when such an optical fiber is used as the light-guiding fiber 2. More generally, the first invention is also effective when protecting the relatively long light-guiding fiber 2, which guides the laser beam from the laser generation source 90 to the laser treatment device, such as a laser handpiece, against the moisture and when attempting to extend the service life of the light-guiding fiber 2.

For this kind of the light-guiding fiber 2, glass fibers, such as chalcogenide and quartz glass fibers, as well as crystal glass Fibers, such as sapphire and zinc selenium fibers can be used.

The probe 21 described below is not limited to a fiber probe. Furthermore, the laser treatment device of the first invention is not limited to a dental handpiece. Moreover, the example described above can be modified in many ways. As a modification example of the handpiece shown in FIG. 3, the entire internal diametric section of the handpiece unit 1 can be used as an air passage. For the light-guiding fiber 2, an optical fiber having high light-guiding efficiency can be selected without worrying about resistance against water and moisture.

Next, an example wherein the fiber probe 21 used in the second invention is used for the irradiation probe of the first invention is described below together with an example of a water supply means which supplies water to the leading end of the probe of the second invention.

The fiber probe 21 shown in FIGS. 1 to 3 is used to guide the laser beam guided by the above-mentioned light-guiding fiber 2 to the object to be irradiated and comprises a short thin optical fiber. Since the fiber probe 21 is short, even though the light guiding efficiency thereof is inferior to that of the fluoride fiber used for the light-guiding fiber 2, the probe can comprise an optical fiber which is superior to the fluoride fiber in moisture resistance and mechanical strength such as resistance against breakage.

Additionally, the fiber probe 21 is desired to be low in cost because of the following reasons: the probe melts due to the heat generated when the laser beam is irradiated from the laser beam emission end thereof; the substances transpired from the living tissues during irradiation attach to the emission end; and the probe must be replaced relatively frequently. For these reasons, it is desired that the optical fiber for the fiber probe 21 has a core and a clad made of quartz glass and is covered with a metal coating or a protection jacket made of heat resistant resin, such as polyimide. Moreover, since the fiber is replaced relatively frequently as described above, the use of a fluoride fiber is not rejected.

To accommodate the fiber probe 21 at the leading end of the handpiece 1, the above-mentioned joint 11 has a probe insertion hole 13 communicating with an incident cooling chamber 14. The insertion hole has a small diameter section 131, a large diameter section 132 and a step section 133 provided at the boundary of the small and large diameter sections. The trailing end of the fiber probe 21, with the protection jacket removed, is inserted into the small diameter section 131. The fiber probe 21 is inserted into the large diameter section 132, with the external circumference of the probe being coated with a trailing end sleeve (ferrule) 22. When the end section of the trailing end sleeve 22 contacts the step section 133, the incident end 211 of the fiber probe 21 is positioned so that the incident end 211 projects into the incident cooling chamber 14 by an appropriate length.

Although the emission end 201 and the incident end 211 are designed and arranged such that the laser beam emitted from the emission end 201 of the light-guiding fiber 2 enters the incident end 211 of the fiber probe 21 as efficiently as possible, a part of the laser beam emitted from the emission end 201 is lost and generates heat. To cope with this heat, the emission end 201 is cooled by the dry gas supplied from the first air supply pipe 3 and the incident end 211 is cooled by the gas supplied from the above-mentioned second air supply pipe. This air supply prevents the emission end 201 and the incident end 211 from being stained with dust.

The second air supply pipe 4 for supplying gas to cool the incident end 211 of the fiber probe 21 passes through the light-guiding fiber holder 6 and the light-guiding shield plate holder 82 and is inserted into a pipe insertion hole 15A and the opening end section of the second air supply pipe 4 is secured by adhesive for example. The gas (usually air) supplied from the second air supply pipe 4 passes through air supply passages, that is, the pipe insertion hole 15A and an air supply passage 15B, then enters the incident cooling chamber 14 to cool the incident end 211. The gas entered the incident cooling chamber 14 reaches a gas discharge passage 15D via a gas passage 15C and is discharged from the gas discharge port 124 of the cover nut 12 to the outside. It is not necessary to use dry air as the gas to be supplied from the air supply pipe 4 used to cool the incident end 211 of the probe 21.

The joint 11 has a small diameter section on the leading end side thereof and is equipped with a screw section 19 on the leading end side of the external circumference thereof. When the screw section 102 of the cover nut 12 is tightened, the step section 18 provided at the boundary of the large and small diameter sections contacts the step section 122 of the leading end section of the cover nut 12 to secure the joint 11 and the related parts to the handpiece unit as described above.

Numeral 24 represents a probe holder. The screw 27 provided inside the large diameter section 25 thereof engages the above-mentioned screw 19. The taper section 28 provided inside the probe holder 24 has, on one end side thereof, a tapered surface matching to the tapered section 28. On the other end thereof, the taper section 28 engages a fixture 23 contacting the external diameter surface of the leading end of the joint 11. When the holder 24 is moved to the left in the figure by tightening the screw 27 of the probe holder 24, the taper section 28 presses the tapered surface of the fixture 23, thereby deforming the fixture 23 inward, securing and holding the trailing end sleeve 22 of the fiber probe 21, When the screw 27 of the fixture 24 is loosened, the trailing end sleeve 22 secured by the fixture 23 is released. In this way, by tightening and loosening the screw 27 of the fixture 24, the fiber probe 21 equipped with the leading end sleeve 22 can be attached and detached as desired.

The external surface of the small diameter section 26 of the probe holder 24 has a polygonal shape such as a hexagon and is covered with the polygonal base end section 291 of the probe protection pipe 29. The water supply pipe 5 passes through the light-guiding fiber holder 6 and the light-guiding shield plate holder 82 and is inserted into the water supply pipe insertion hole 16A of the joint 11, and the opening end section of the pipe is secured by adhesive for example. The leading end of the insertion hole 18A is communicated with a water passage 16B opened to the leading end surface of the joint 11.

The water (salt water or sprayed water can also be used) supplied From the water supply pipe 5 passes through the water passage 16B, the internal space of the tightening ring 23 and slit grooves 221 provided in the longitudinal direction of the leading end side of the trailing end sleeve and enters the space between tile small diameter section 26 of the probe holder 24 and the fiber probe 21, then flows along the water passage provided in a gap 16C between the internal surface of the probe protection pipe 29 and the external surface of the fiber probe 21. The water is then blown out to teeth and their peripheral portions to remove residues generated after transpiration and attaching to the teeth and their peripheral portions. At this time, the leading end of the fiber probe is also cooled and cleaned. Furthermore, since the water flows along the fiber probe 21 as described above, the fiber probe 21 is also cooled.

Although the above-mentioned example shows a structure wherein the emission end 201 of the light-guiding fiber and the incident end 211 of the fiber probe are equipped with the cooling chambers 81 and 14 respectively, the present invention is not limited to this structure. The front surfaces of the emission end 201 and tile incident end 211 can be used as gas passages communicating with the first air supply passage 3 and the second air supply passage 4 respectively. Like the above-mentioned structure, this structure can also accomplish the same objects, that is, mutual isolation and moisture prevention.

EXAMPLE 2

Next, FIG. 4 shows examples of various shapes of the fiber probe 21 applied to the laser treatment device, more particularly to the dental laser treatment device of the second invention. The shape of the fiber probe shown in FIG. 1 is a general use type having a uniform outer diameter throughout its length up to both ends thereof. The fiber probe 21 shown in FIGS. 4(A) and 4(B) has a conical section 215 tapered off toward the leading end thereof. By making the diameter of the leading end smaller, the irradiation end surface can reach the deep bottom section of the small diameter section of the tooth to be treated for example so that the inside of a pulp canal for example can be treated by converging the laser beam. In the figures, numeral 213 represents a glass fiber, numeral 214 represents a protection clad and numeral 22 represents the trailing end sleeve (ferrule) described before. FIG. 4(B) shows a flexible fiber whose tapered section is in a bent condition when it is used. FIG. 4(C) shows an example wherein an extremely thin cylindrical column 218 is extended from the leading end of the conical section 215.

Figure 4A:
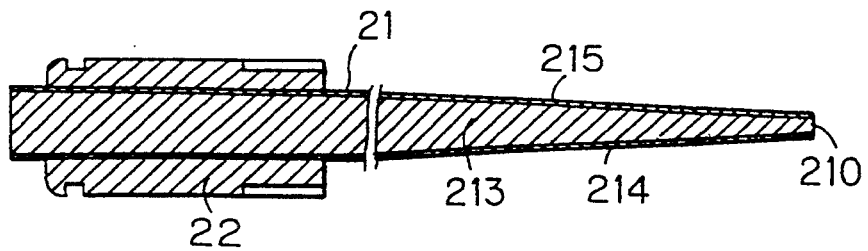
FIGS. 4(A) to 4(F) are views illustrating various shapes of fiber probes replaceably installed at the leading end of the laser handpiece of the second invention.
Figure 4B:
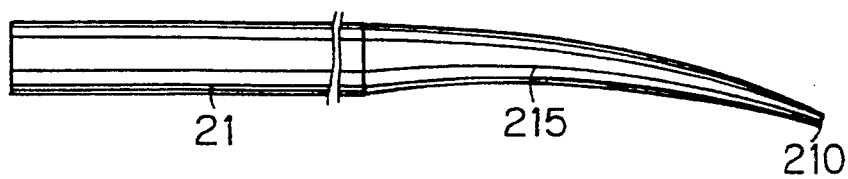
Figure 4C:
Figure 4D:
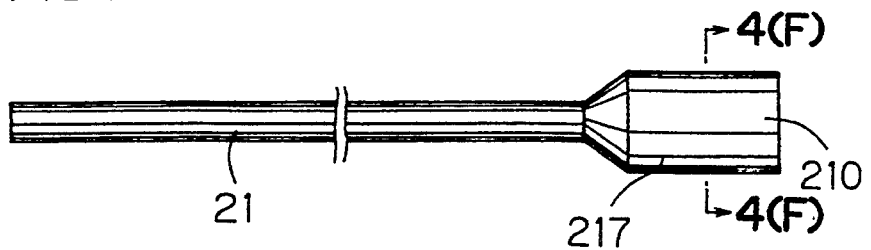
Figure 4E:
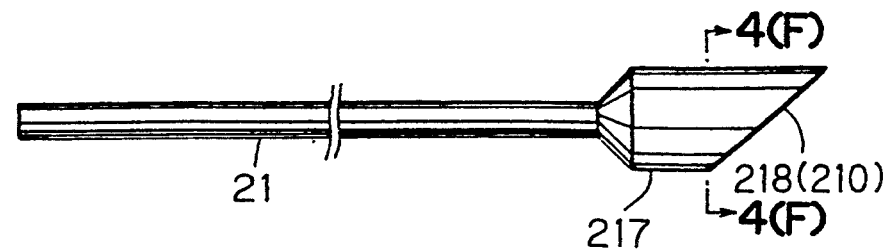
Figure 4F:
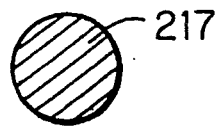

The examples of the fiber probe 21 shown in FIGS. 4(D) and 4(E) have expanded diameter sections 217. The expanded vertical irradiation end surface 210 or the expanded slant irradiation end surface 218 of the fiber probe 21 is contacted to the affected portion so that the laser beam is irradiated widely and uniformly. These examples are used effectively to treat initial dental caries, to provide acid resistance to tooth surfaces and to perform etching.

The irradiation end surface 210 of the fiber probe 21 is not limited to a flat surface but can have a convex or concave surface to set the expansion angle of the laser beam as desired. In addition, the irradiation end surface 210 is not necessarily required to be a ground smooth surface but can have an appropriate rough, bent-open or cleaved surface.

Figure 5A:
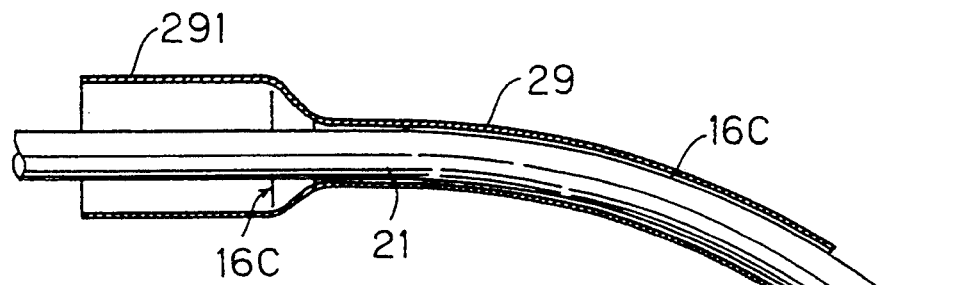
FIGS. 5(A) to 5(F) are views illustrating various shapes of probe protection pipes to be fit over the fiber probes.

FIGS. 5(A) to 5(E) show the relationship between various shapes of the probe protection pipe 29 and the fiber probe 21. FIG. 5(A) shows an example of the probe protection pipe 29, the leading end of which is bent. Since the fiber probe 21 inserted into the probe protection pipe 29 is restricted by the internal surface of the probe protection pipe 29 when the fiber probe 21 is bent, the direction and angle of the fiber probe 21 can be adjusted as desired by changing the curvature and length of the probe protection pipe 29. Numeral 291 represents the base end section described before.

Figure 5B:
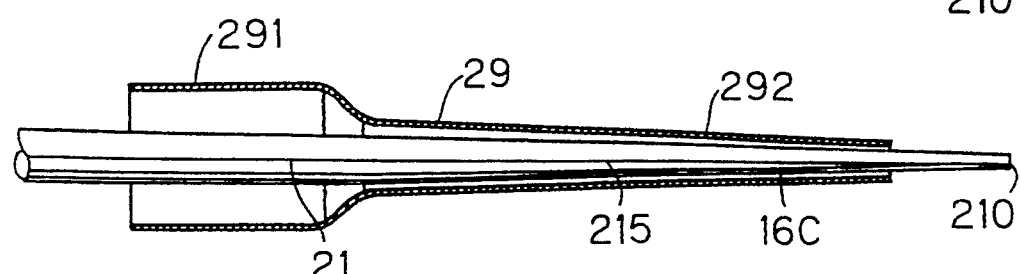
Figure 5C:
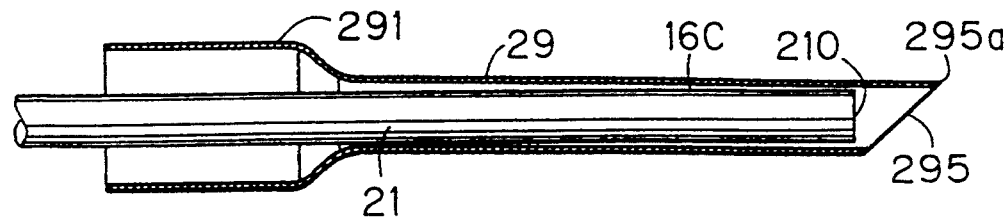

FIG. 5(B) shows an example having a probe protection pipe 292 and a glass fiber 215, both being tapered off toward their leading ends so that they match the above-mentioned tapered fiber probe 21 (FIG. 4(A)). The probe protection pipe 29 shown in FIG. 5(C) has an end surface 295 oblique to the axis thereof. The laser beam is irradiated intensely to the oblique surface side and the amount of irradiation in the direction of the pointed end 295a of the oblique surface can be reduced. This type of the probe protection pipe 29 is used to remove subgingival calculus to be treated. When the pointed end 295a on the leading end side of the probe protection pipe 29 is directed to the tooth side, the cement and dentin of the tooth are less damaged. On the contrary, when the pointed end 295a is directed to the gum side, the adverse effect of laser irradiation to the gum section can be reduced.

Figure 5D:
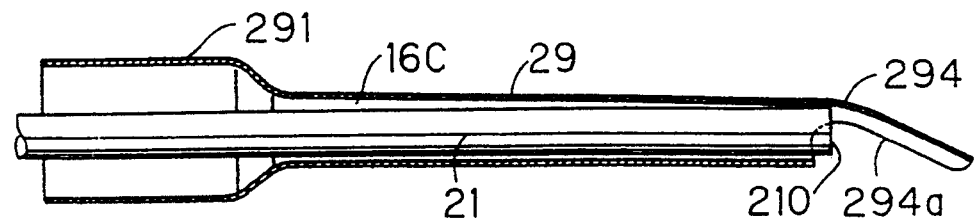

FIG. 5(D) shows an example of the probe protection pipe 29 equipped with an inclined pointed tongue 294 at the leading end section, whose inside surface, that is, the surface to be projected by the laser beam irradiated from the leading end 210 of the fiber probe, has a mirror surface 294a so that the laser beam is reflected by the mirror surface 294a to change the direction of the laser beam. The probe protection pipe 29 comprises a stainless steel pipe or other metal pipe having high reflection performance. The mirror surface 294a can be provided with reflection coating such as gold plating.

Figure 5E:
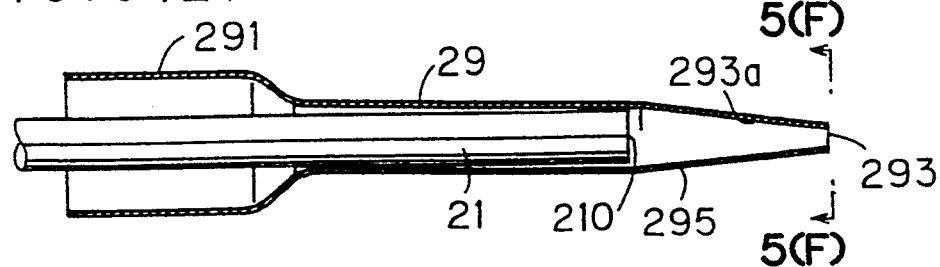
Figure 5F:
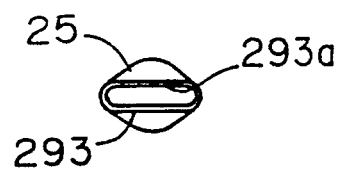

FIG. 5(E) shows an example of the probe protection pipe 29, whose leading end section 29D has a narrow flat shape and accommodates the irradiation end surface 210 of the fiber probe 21. The inside surface 293a of the flat pointed end section 295 of the probe protection pipe 29 is gold-plated for example to enhance the reflection performance thereof. This type of the probe protection pipe 29 is effective to remove tartar from the periodontal tissues without damaging the cement of the tooth.

Figure 6A:
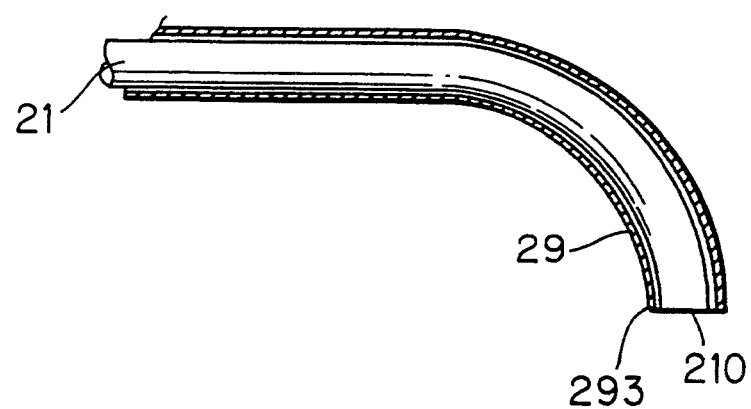
FIGS. 6(A) and 6(B) are sectional views of specially bent probe protection pipes.
Figure 6B:
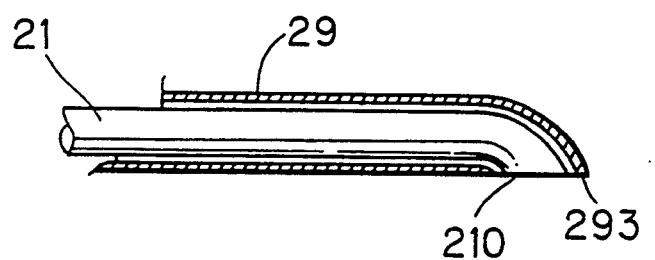

FIGS. 6(A) and 6(B) show examples wherein the leading end 293 of the bent probe protection pipe 29 is almost flush with the irradiation end surface 210 of the fiber probe 21 inserted into the probe protection pipe 29. Since the irradiation end surface 210 does not project beyond the probe protection pipe 29, the irradiation area of the probe can be limited and the danger of fiber breakage is reduced. The fiber probe 21 shown in FIG. 6(B) can also be used in the same way as that shown in FIG. 5(C).

EXAMPLE 3

Figure 7:
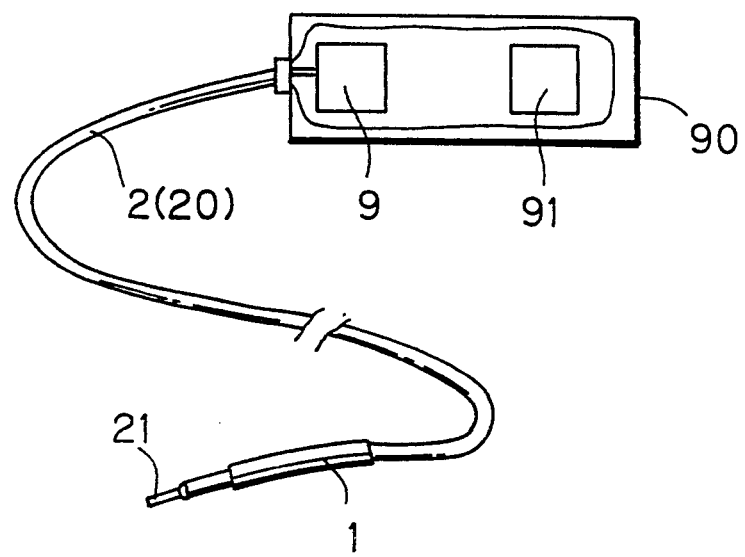
FIG. 7 is an external view of a dental laser treatment device illustrated as an example of the third invention.

Examples of the third invention are then described below. FIG. 7 is an external view of the dental laser treatment device of the third invention. This device comprises an Er:YAG solid laser generator 9 accommodated in a laser generator 90 and a laser control means 91 for controlling the laser output of the laser generator 9.

A fluoride light-guiding fiber 2 having extremely little absorption loss for the Er:YAG solid laser beam is connected to the laser generator 90 and is also connected to the handpiece unit 1 detailed before. At the leading end of the handpiece unit 1, the fiber probe 21 is projected and installed.

The laser control means 91 controls the laser output in the pulse width range of 150 to 300 μs, in the pulse period range of 1 to 30 pps and at the maximum irradiation energy per pulse of 1 J. If the pulse width exceeds the above-mentioned upper limit value, the fluoride light-guiding fiber may be damaged. If the pulse width is smaller than the lower limit value, the tooth tissue is stimulated by heat. If the pulse period exceeds the upper limit value, the laser generator is required to be made larger, having the disadvantage of being expensive. If the pulse period is smaller than the lower limit value, tile cut-off speed of the device is reduced particularly, lowering the efficiency of the device. If the irradiation energy exceeds the maximum value of 1 J per pulse, the light-guiding fiber may be damaged or may have less durability.

Figure 8:
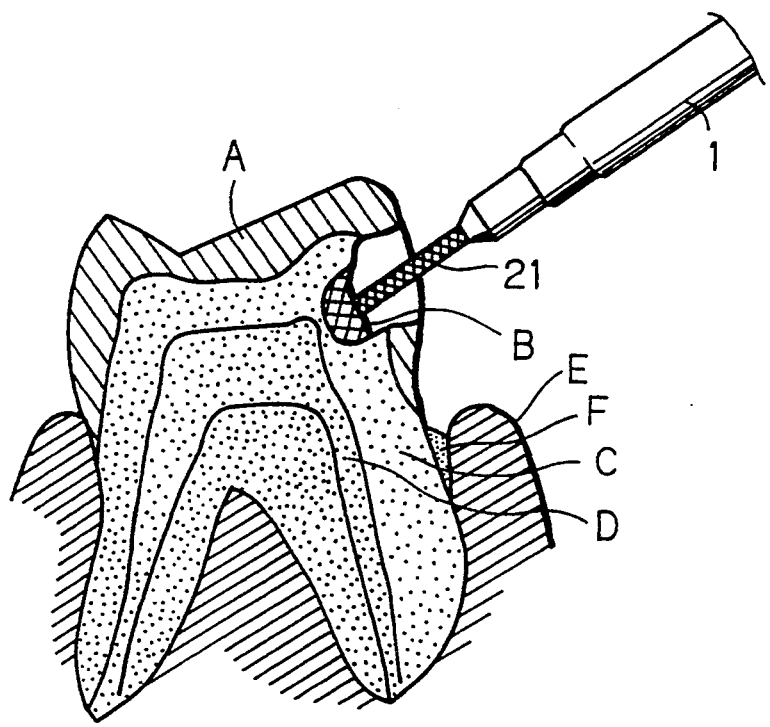
FIG. 8 shows a tooth portion to be treated by the laser treatment device shown in FIG. 7.

As shown in FIG. 8, the laser treatment device of the third invention is used to treat enamel A, area of dental caries B, dentin C, dental pulp D and tartar F at the periodontal area of the tooth to be treated. Laser irradiation conditions differ depending on the irradiation positions. The examples of the laser irradiation conditions are described below.

When removing transpiration residues from soft dentin B and enamel A at an area of dental caries and when removing transpiration residues from normal dentin C to form a cavity, efficient cut-out was possible by using a quartz fiber having a core diameter of 600 μm in the irradiation output range of 100 to 200 mJ (per pulse) and at a pulse period of 5 pps on the irradiation end surface 210 of the fiber probe 21 while water was poured. When removing transpiration residues from normal dentin C, the cutting speed of the device was able to be further increased by raising the output to about 200 mJ, enhancing the efficiency of the device.

Etching was possible by irradiating the laser beam to enamel A in the low energy density range of about 5 to 20 mJ/cm$^2$ as a pretreatment for resin filling after cavity formation. This etching was thus able to be replaced with the conventional acid etching method.

When removing tartar F located above and below the fringe of gum E, which causes periodontal disease, a fiber having a core diameter of 600 μm was contacted to tartar F and the laser beam was irradiated in the irradiation output range of 20 to 30 mJ (per pulse) and at a pulse period of 5 pps while water was poured. Since the laser beam irradiated from the fiber probe 21 was superior in directivity and convergence, tartar F was able to be removed completely without damaging the cement located just under tartar F.

FIGS. 9(A) to 9(E) show examples of the fiber probe 21. In the fiber probe shown in FIG. 9(A), a light-guiding straight fiber (core section) 41 is covered with a clad layer 44, and the external surface of the clad layer 44 is covered with a reinforcing coating 214 described before.

The fiber (core section) 41 is made of a quartz fiber having high water resistance. When used to cut off tooth substance, the fiber having a diameter of 50 to 600 μm is suited. The fiber can have a tapered shape with a different sectional area. In this case, the diameter at the end surface 210 on the fiber irradiation side is set in the range of 50 to 600 μm.

Figure 9A:
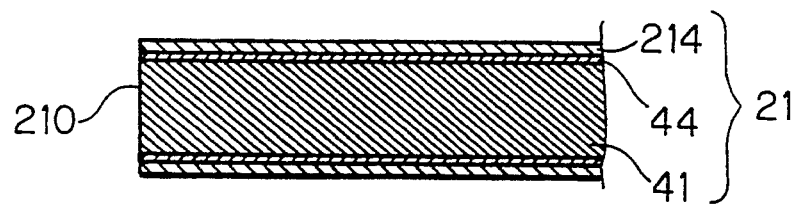
FIG. 9(A) is a sectional view of a fiber probe illustrated as another example of the irradiation probe used for the dental laser treatment device of the third invention.
Figure 9B:
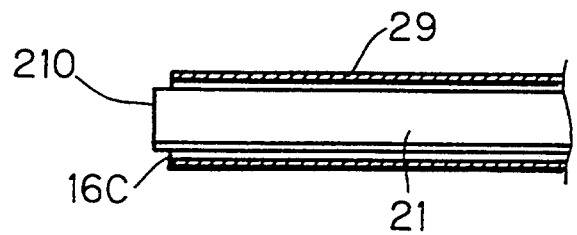
FIGS. 9(B) and 9(C) are sectional views of third and fourth examples of probe protection pipes used for the device of the third invention.

FIG. 9(B) shows an arrangement of the leading end section of the probe protection pipe 29 covering the external surface of the fiber probe 21. In this arrangement, the irradiation end surface 210 is disposed so that it slightly projects beyond the probe protection pipe 29 and water can be poured from the water passage of the gap 16C in the laser irradiation direction.

Figure 9C:
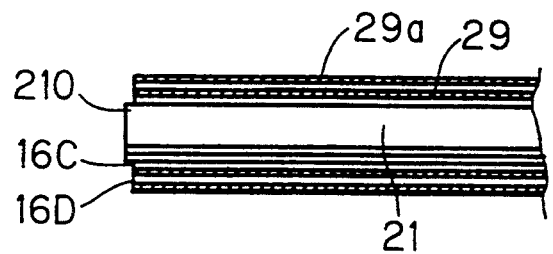

In FIG. 9(C), dual probe protection pipes 29 and 29a are coaxially fit over the external surface of the fiber probe 21. The gaps 16C and 16D between the pipes are used to supply water and to discharge air respectively. With this structure, the water and air are discharged as mist in front of the laser irradiation position, thereby being effective for cooling irradiated portions and for removing transpiration residues.

Figure 9D:
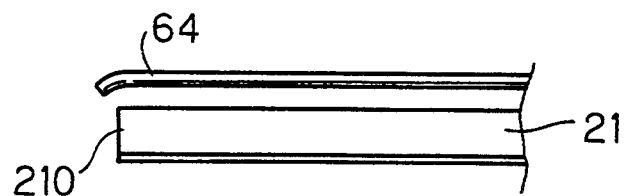
FIGS. 9(D) and 9(E) are side views of fifth and sixth examples of fiber probes with water pouring pipes installed along the probes.
Figure 9E:
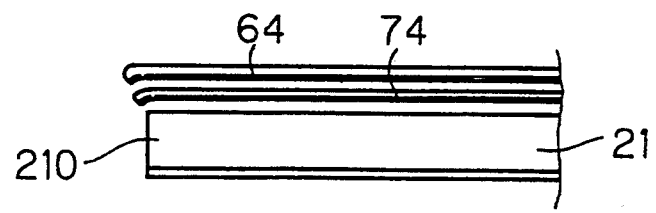

FIGS. 9(D) and 9(E) show examples wherein a small diameter water supply pipe 64 is disposed parallel to the fiber probe 21 independently of or together with an air supply pipe 74, without using any probe protection pipe. The water supply pipe 64 is connected to the water supply passages 5 and 16B described before and the air supply pipe 74 is also connected to the above-mentioned second air supply passages 4 and 15C so that the water and air supply pipes blow out water and air forward respectively.

As understood from the above-mentioned descriptions, the first, second and third inventions can fully accomplish the above-mentioned first, second and third objects and can offer advantages For enhancing the feasible validity of the laser treatment device.

We claim:

1. A medical laser treatment device comprising a laser generation source and a laser handpiece which comprises a light-guiding fiber coupled to said laser generation source for guiding a laser beam irradiated from said laser generation source, a probe provided at one end of said laser handpiece with an incident end of said probe adjacent to an emission end of said light-guiding fiber for guiding the laser beam to an object to be irradiated, at least two independent first and second air supply passages and at least one water supply passage provided in said handpiece, a light-guiding shield member airtightly coupled to said laser handpiece such that the emission end of said light-guiding fiber is airtightly isolated from the incident end of the probe, and wherein said first air supply passage extends to said emission end of said light-guiding fiber so that dry gas supplied from said first air supply passage cools the emission end of said light-guiding fiber and said second air supply passage extends to said incident end of said probe so that gas supplied from said second air supply passage cools the incident end of said probe, and said water supply passage extends toward a peripheral section of a leading end of said probe such that water supplied from said water supply passage is blown out from the peripheral section of the leading end of said probe.

2. A medical laser treatment device according to claim 1, further comprising a means for flowing backward the dry gas used to cool the emission end of said light-guiding fiber in the section incorporating said light-guiding fiber and discharging said dry gas at a position fully away from the emission end of said light-guiding fiber.

3. A medical laser treatment device according to claim 1, wherein said light-guiding fiber is a fluoride fiber.

4. A medical laser treatment device according to claim 1 wherein a base section of a probe protection pipe is removably fitted and connected to a front section of said handpiece such that water from said water supply passage passes through a gap between an internal surface of said probe protection pipe and an external surface of said probe to supply water to a leading end of said probe.

5. A medical laser treatment device according to claim 4, wherein said probe is tapered off toward the leading end thereof and the emission end surface thereof intersects an axis of said fiber orthogonally.

6. A medical laser treatment device according to claim 4 wherein said probe protection pipe is metal pipe which is straight.

7. A medical laser treatment device according to claim 4, wherein the leading end of said probe protection pipe has a cut-off surface orthogonal to an axis probe protection pipe.

8. A medical laser treatment device according to claim 4, wherein a pointed tongue having a mirror surface on an internal surface of said pointed tongue protrudes obliquely to an axis of said protection pipe at the leading end of said protection pipe.

9. A medical laser treatment device according to claim 4, wherein the leading end of said probe protection pipe is flat.

10. A medical laser treatment device according to claim 4, wherein said probe is expanded toward the leading end thereof and the emission end surface thereof intersects an axis of said fiber orthogonally.

11. A medical laser treatment device according to claim 4, wherein said probe is expanded toward the leading end thereof and the emission end surface thereof intersects an axis of said fiber obliquely.

12. A medical laser treatment device according to claim 4, wherein said probe is tapered off toward the leading end thereof and the emission end surface thereof intersects an axis of said fiber obliquely.

13. A medical laser treatment device according to claim 4, wherein said probe protection pipe is metal and tapered off toward the leading end thereof.

14. A medical laser treatment device according to claim 4, wherein said probe protection device is a metal pipe which is bent.

15. A medical laser treatment device according to claim 4, wherein said probe protection pipe is a synthetic resin pipe which is straight.

16. A medical laser treatment device according to claim 4, wherein said probe protection pipe is a synthetic resin pipe which is tapered off toward the leading end thereof.

17. A medical laser treatment device according to claim 4, wherein said probe protection pipe is a synthetic resin pipe which is bent.

18. A medical laser treatment device according to claim 1 or claim 4, wherein said laser generation source is a laser generator for generating an Er:YAG solid laser beam, said light-guiding fiber is a fluoride fiber and said medical laser treatment device is equipped with a laser control means for adjusting the laser output of said laser generator.

19. A medical laser treatment device according to claim 18, wherein the diameter of the leading end of said probe is in the range of 50 to 600 $\mu$m, and the laser irradiation output obtained at the leading end of said probe can be adjusted in the pulse width range of 150 to 300 $\mu$s, in the pulse period range of 1 to 30 pps and at the maximum irradiation energy per pulse of 1 J by said laser control means.

* * * * *